United States Patent [19]
Schaldach

[11] Patent Number: 5,603,725
[45] Date of Patent: Feb. 18, 1997

[54] CIRCUIT FOR MEASURING IMPREDANCE IN THE HEART

[75] Inventor: Max Schaldach, Erlangen, Germany

[73] Assignee: Biotronik Mess- und Therapiegeraete GmbH Ingenieurbuero Berlin, Berlin, Germany

[21] Appl. No.: 403,699

[22] PCT Filed: Sep. 16, 1993

[86] PCT No.: PCT/DE93/00888

§ 371 Date: Mar. 17, 1995

§ 102(e) Date: Mar. 17, 1995

[87] PCT Pub. No.: WO94/06512

PCT Pub. Date: Mar. 31, 1994

[30] Foreign Application Priority Data

Sep. 17, 1992 [DE] Germany .......................... 42 31 602.2

[51] Int. Cl.[6] .................................................... A61N 1/362
[52] U.S. Cl. ................................................................ 607/11
[58] Field of Search .............................. 607/11, 12, 13, 607/17–24; 128/696, 734

[56] References Cited

U.S. PATENT DOCUMENTS

| 3,871,359 | 3/1975 | Pacela . |
| 3,874,368 | 4/1975 | Asrican . |
| 4,702,253 | 10/1987 | Nappholz et al. . |

FOREIGN PATENT DOCUMENTS

| 0134908 | 3/1985 | European Pat. Off. . |
| 0140472 | 5/1985 | European Pat. Off. . |
| 0151689 | 8/1985 | European Pat. Off. . |
| 0327292 | 8/1989 | European Pat. Off. . |
| 0449401 | 10/1991 | European Pat. Off. . |
| 139518 | 1/1980 | Germany . |
| 3629587 | 3/1987 | Germany . |

OTHER PUBLICATIONS

G. Boheim et al.: "Intrakardiale Impedanzmessung zur Regelung frequenzadaptiver Schrittmachersystems", In: Biomedizinische Technik, vol. 32, Sep. 1987, Berlin, Germany, pp. 41–42.

*Primary Examiner*—William E. Kamm
*Assistant Examiner*—Scott M. Getzow
*Attorney, Agent, or Firm*—Spencer & Frank

[57] ABSTRACT

A circuit for determining the impedance in a heart having a pacemaker electrode to which voltages are applied disposed in the ventricle chamber thereof. The circuit uses the pacemaker electrode. The circuit includes a current source operatively connected to the pacemaker electrode to apply current thereto, the current source having a current direction which can be switched. Switching circuitry is provided for switching the current direction of the current source. The voltage applied to the pacemaker electrode at different measuring times is measured with measuring circuitry. A value representative of the impedance in the heart is determined from a difference between the voltages applied to the pacemaker electrode at two of the different measuring times measured by the measuring circuitry. Currents having an identical magnitude but having opposite directions are applied to the pacemaker electrode by the current source which is switched by the switching circuitry at the two respective measuring times.

8 Claims, 5 Drawing Sheets

CIRCUIT FOR MEASURING IMPREDANCE IN THE HEART

BACKGROUND OF THE INVENTION

1. Field of the Invention

The invention relates to an arrangement for for determining the impedance in the heart by way of the pacemaker electrode disposed in the ventricle chamber.

2. Background Information

In some cases it is favorable to determine the electrical impedance in the heart region, using measuring technology, during operation of pacemakers, particularly in connection with an adaptation of the stimulation rate to the instantaneous stress on the patient.

It is known, for example, to determine the cardiac stroke volume in the manner of impedance plethysmography, i.e., by means of a measurement of the impedance in the heart. To do this, in the simplest case two electrodes are inserted into the heart. If a current of a known magnitude flows through the cardiac volume via these electrodes, the impedance in the heart can be determined by means of a voltage measurement. A corresponding apparatus for measuring the ventricular volume is described in DE-36 29 587-A1. This type of arrangement is not suitable for use in pacemakers.

From EP-A-0 140 472, a pacemaker is known in which the impedance in the heart is measured by way of further electrodes disposed at the pacemaker electrode, and the stimulation rate is controlled with the stroke volume determined from this. In this case, a series of measurements is provided from whose average value the stroke volume is calculated, which however, has disadvantages.

SUMMARY OF THE INVENTION

The object of the invention is to disclose an arrangement of the generic type mentioned at the outset, which is particularly suited for use in pacemakers.

This object is accomplished with the characterizing features of the invention, as will be described below.

The invention is based on the recognition that, in impedance measurements in the heart which ultimately always amount to combined current/voltage measurements, it is important to eliminate, if possible, the interference voltages occurring there, of which, among other things, a polarization voltage stemming from the stimulation pulse can be a part. This must take place with the smallest possible energy expenditure because of the limited battery charge.

In the circuit according to the invention, the pacemaker electrode is connected to a current source that can be switched in its current direction and be controlled with respect to its current intensity. The voltage applied to the pacemaker electrode is measured by at least one voltage measurement apparatus.

Measurement is particularly effected outside of the times of the stimulation pulses or the times that must be available for detection of the signals emitted by the heart.

If a voltage not stemming from the current flow is present at the pacemaker electrode, this voltage makes a corresponding contribution to the measured voltage, i.e., this voltage measurement is erroneous. This measuring error is eliminated by the reversal of the current direction by means of corresponding switching means, and the remeasurement of the voltage applied to the pacemaker electrode. In this measurement, the voltage not stemming from the current flow makes the same contribution as in the first measurement. In the subtraction of the two measured voltages, these contributions cancel each other out, while the non-erroneous components are added, because their operational signs are reversed by the current reversal.

The currents necessary for measurement need not be made so large in this way that the voltage dropoff caused by them, which takes place at the impedance, is significantly greater than the polarization voltage. This leads to an increased service life of the pacemaker battery.

In an advantageous modification of the invention, the magnitude of the current delivered by the current source and flowing by way of the pacemaker electrode is controlled as a function of the difference between the voltages measured consecutively in the currentless state. In this way the intensity of the current can be optimally adapted to the interference level, which cannot be compensated, leading to a further relief of the pacemaker battery.

In an advantageous manner, the delivery of current by the current source is effected in the form of pulse packets, with each pulse packet comprising two sequential rectangular pulses. This combines numerous advantages: on the one hand, the energy requirement for measurement decreases significantly; on the other hand, in an impedance that changes temporally in this manner, which is the case of the beating heart, the instantaneous values of the impedance can be measured. These values are more precise than those obtained through long averaging, because the external voltage not caused by the measuring current only changes slightly in pulses that follow one another directly.

In another advantageous modification of the invention, the individual measurements, i.e., the delivery of the pulse packets, are effected at large time intervals with respect to the time interval between the individual pulses. This limitation to few pulse packets is particularly advantageous in connection with the current intensity, which can be controlled as a function of the interference level. The interference interval increases in linear fashion with the increase in the current, that is, with the current consumption, whereas, in contrast, in statistical averaging the interference interval only increases with the root from the number of measurements, and thus only with the root of the current consumption. This is of greater significance in implantable pacemakers, because a battery change is always associated with an operation.

It is often not necessary to know the absolute value of the impedance in the heart; rather, information about its relative change is sufficient. Such relative measurements are to be performed with significantly greater precision than an absolute measurement, especially when the signals to be measured are very small. In such cases, the measuring circuits themselves could produce errors.

In the circuit of the invention, therefore, first a voltage that is representative of the temporal change in the impedance in the heart is formed by the subtraction from a voltage that is measured at a certain point in time, and is representative of the impedance, of a further voltage that is measured at a later point in time; both of these voltages are obtained through measurements in pulse packets that coincide in their pulse sequence. Erroneous voltages that are possibly added by the circuit itself are eliminated with this measure.

In a further step, the difference voltage obtained in this manner is added with a further difference voltage. This further difference voltage is obtained as above, but by means of voltage measurements of pulse packets having an opposite pulse sequence. In this process, first a voltage having the opposite operational sign is also measured, which sign is reversed again by switching means having an intensity that can be controlled with respect to their operational sign.

Erroneous voltages that are a function of operational sign are now eliminated by the summation of the two difference voltages.

Now a sum of temporal changes in impedance in the heart appears at the output of the circuit; the average temporal change can be determined from this sum through the formation of an average value.

BRIEF DESCRIPTION OF THE DRAWINGS

Advantageous modifications of the invention are set forth in detail below, together with the description of the preferred embodiment of the invention, by way of the figures. Shown are in.

DETAILED DESCRIPTION OF THE PREFERRED EMBODIMENTS

Figure 1:
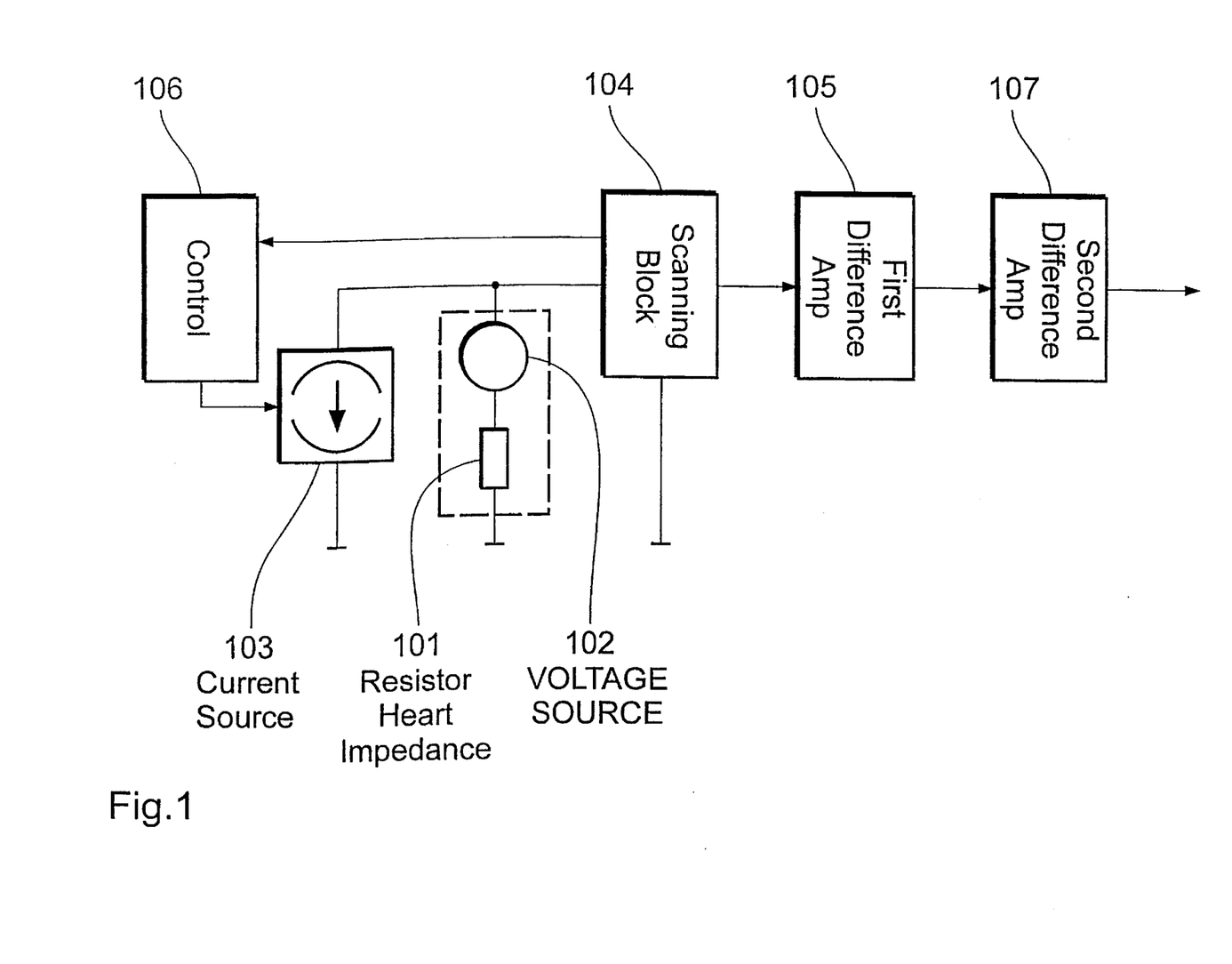
FIG. 1 a block diagram of the embodiment of the invention.

FIG. 1 shows the basic design of the circuit according to the invention in a block diagram. The impedance in the heart to be determined is represented as a resistor 101 having a voltage source 102 connected in series. The voltage source 102 symbolizes the polarization voltage stemming from the pacemaker pulse and other interference voltages. The impedance is charged with a current from a current source 103. The voltage applied to the impedance is detected with a scanning block 104. Its output signal is conducted further to a first difference amplifier 105, whose output signal is determined from the difference between two voltages that were measured at different times by the scanning functional block 104. Moreover, the scanning block 104 is connected to a control 106 which controls the intensity of the current produced by the current source 103 as a function of the instantaneous interference voltage level.

The signal coming from the difference amplifier 105 is conducted further to a second difference amplifier 107. This amplifier forms the difference between two difference voltages of different operational signs. The output signal of the difference amplifier 107 is the output signal of the circuit.

Figure 2:
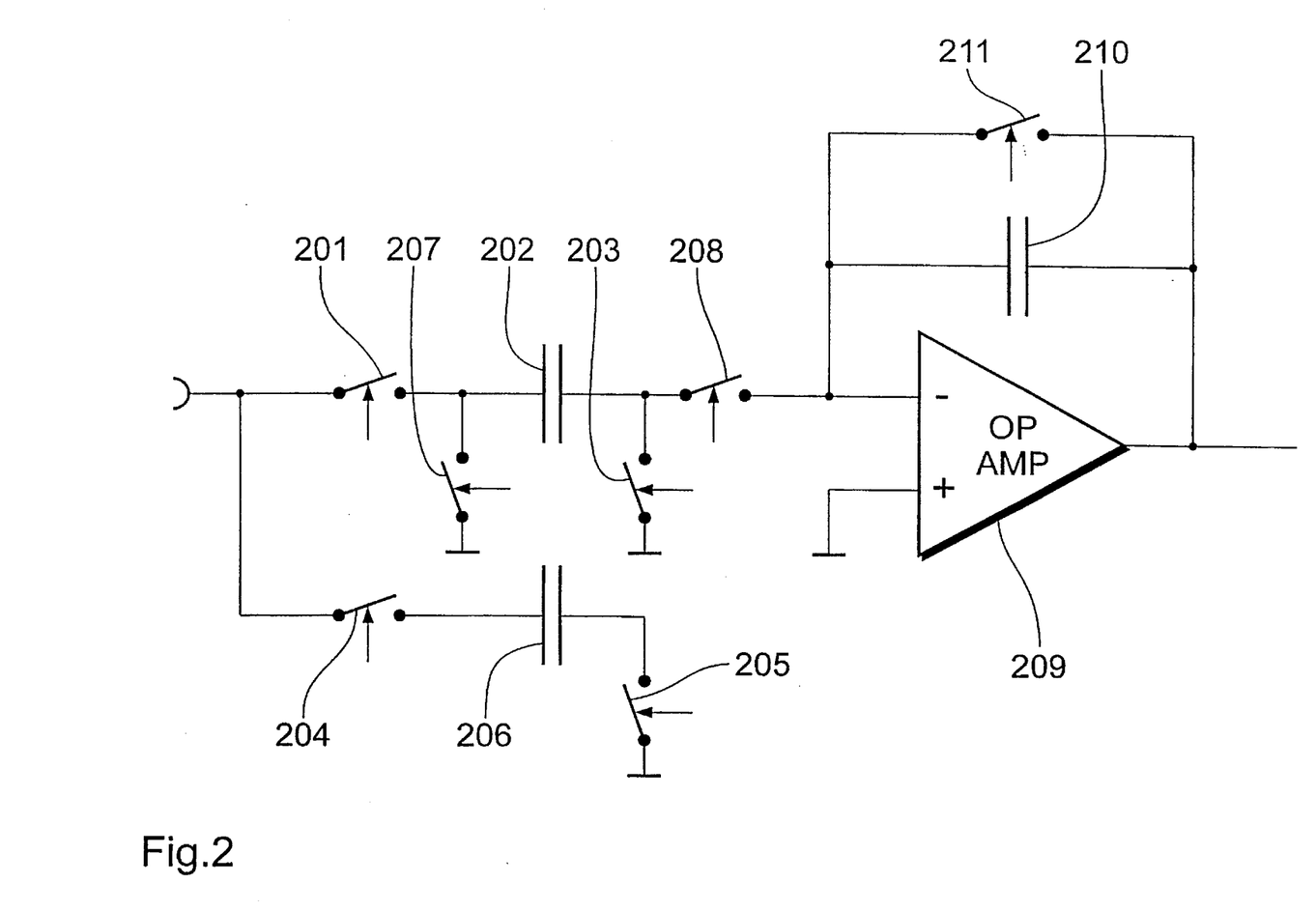
FIG. 2 a block diagram of an input stage of the embodiment according to FIG. 1.

FIG. 2 shows a block diagram of an input stage of the scanning functional block 104. The voltage applied to the impedance in the heart is applied by way of a controllable switch 201 to a capacitor 202 that is connected to ground by way of a further controllable switch. The capacitor is charged by the voltage applied to the impedance.

After a certain period of time, the switches 201 and 203 open, whereupon two further controllable switches 204 and 205 close and a capacitor 206 is charged.

In a further step, the switch 204 opens. Afterwards a controllable switch 207 is closed, together with a further controllable switch 208. The difference between the voltages of the capacitors 206 and 202 is now applied to the input of an operational amplifier 209. A capacitor 210 and a further controllable switch 211 lie in its negative feedback branch.

The operational amplifier, which is wired as an integrator, compensates for the losses occurring because of unavoidable leakage currents of the capacitors 202 and 206, so that a signal that is proportional to the difference of the voltages which are applied to the impedance and measured at different times appears at the output of the input stage.

If these voltages are measured at opposing currents through the impedance, the interference voltages occurring in both cases, which have identical operational signs and are independent of the currents, mutually compensate each other.

The pulses necessary to control the switches are obtained from the clock generator provided in the pacemaker.

Figure 3:
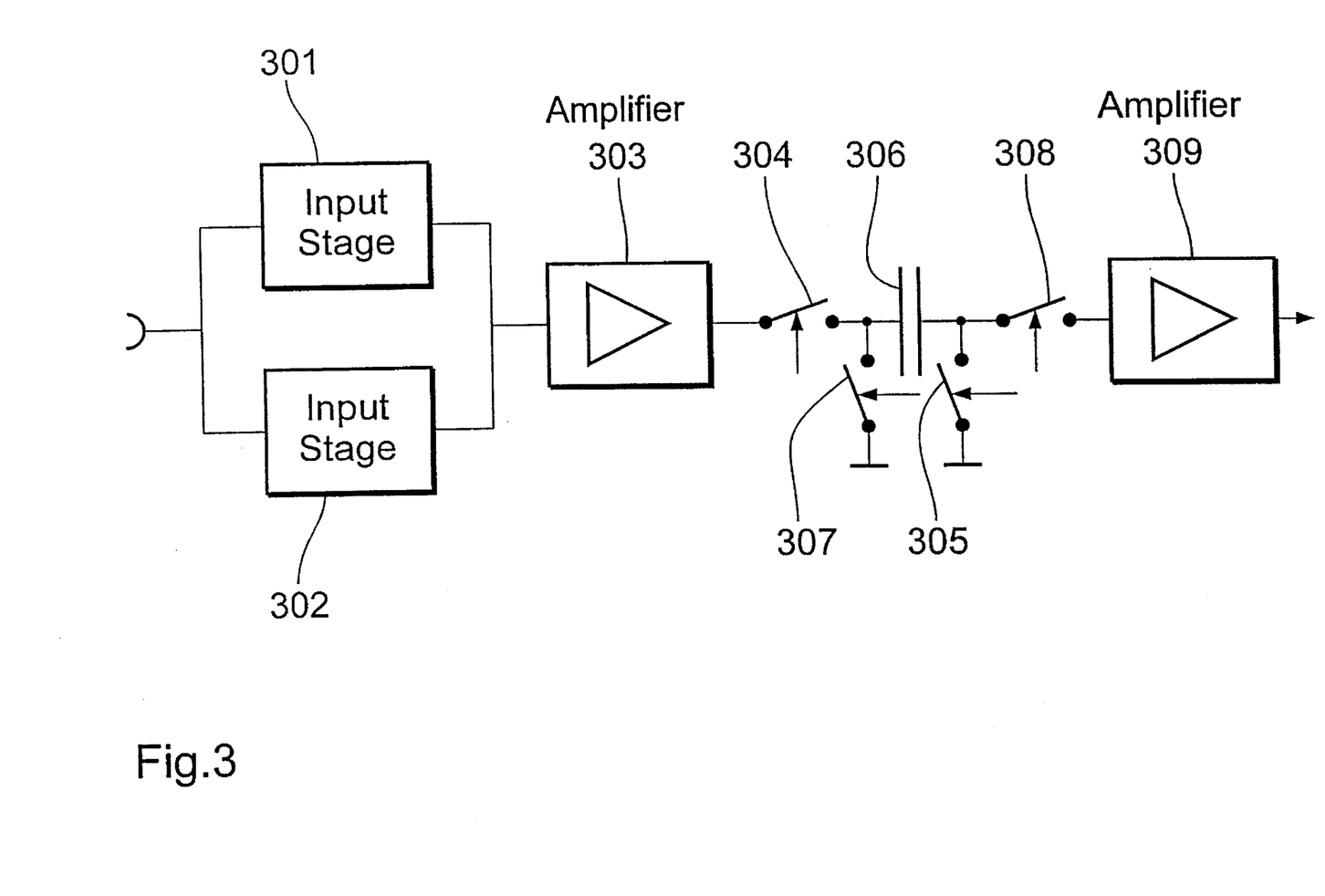
FIG. 3 a portion of the embodiment according to FIGS. 1 and 2.

FIG. 3 shows a portion of the circuit. Two circuit blocks 301 and 302 are located at the input. Each of these blocks represents an input stage of the above-described type. At different times, these blocks deliver output voltages that are representative of the impedance in the heart; these voltages are fed to an amplifier 303.

A capacitor 306 is charged with the amplified signal of the input signal 301 via the switches 304 and 305. With the aid of further switches 307 and 308, the voltage of the capacitor 306 is then applied with a reversed operational sign to the input of a further amplifier 309. The amplified signal of the input stage 302 is again fed to the amplifier 309, with the same operational sign, by way of the switches 304 and 308 via the capacitor 306, so that the difference between the amplified voltages of the input stages 301 and 302 appears at its output.

Figure 4:
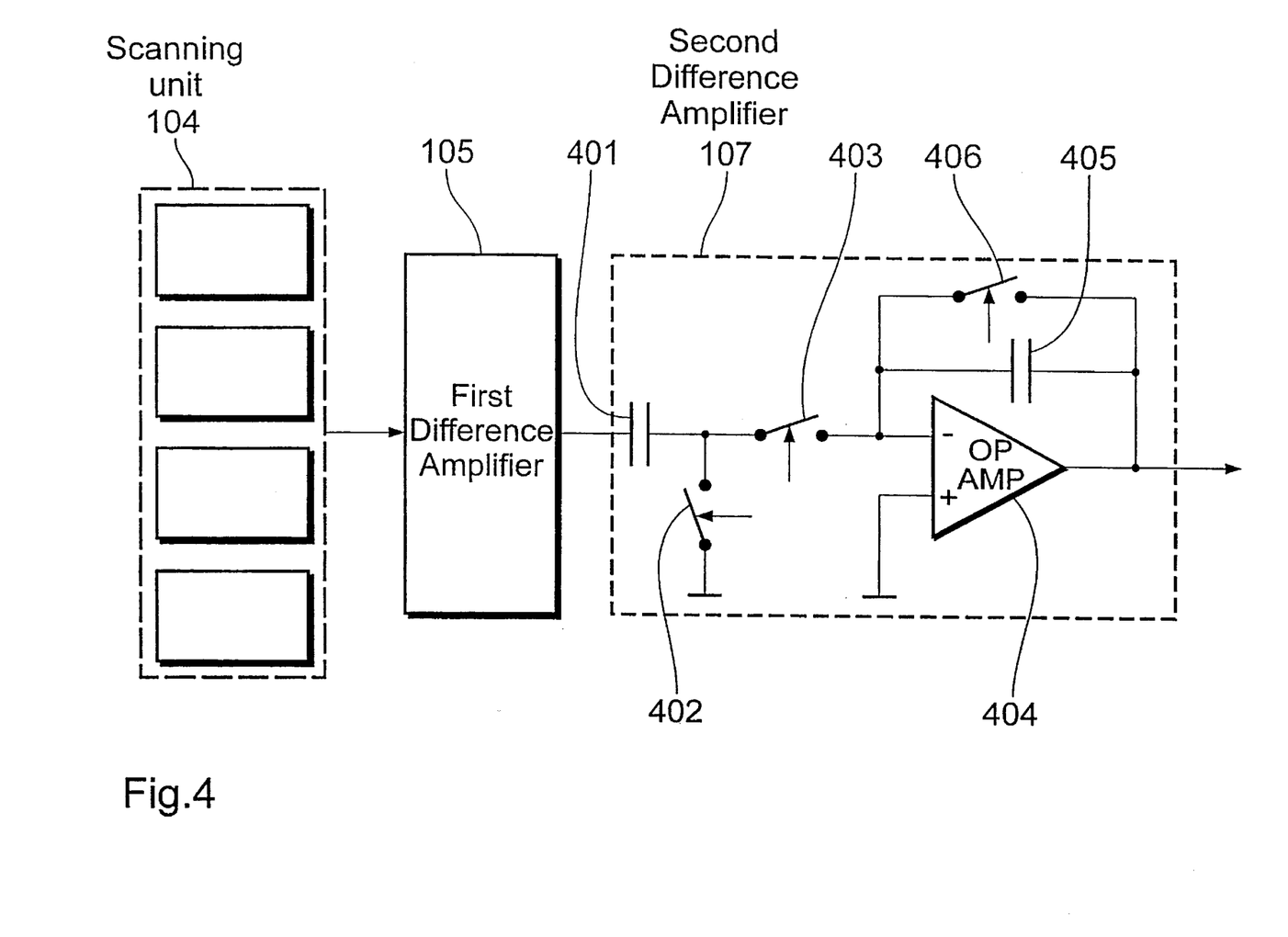
FIG. 4 a block diagram of a portion of the embodiment of the invention according to FIGS. 1 through 3.

FIG. 4 shows a block diagram of the circuit having the scanning unit 104, the difference amplifier 105 and the circuit 107 shown in detail. The difference voltage of two scanning units is applied to a capacitor 401. In the process, a switch 402 is closed. With the aid of a further switch 403, the voltage of the capacitor 401 serves as a reference for a difference voltage of two further input stages of the scanning unit, the voltage having the opposite operational sign. The sum of the two difference voltages appears at the output of an operational amplifier 404, in whose reverse feedback branch a capacitor 405 and a switch 406 lie.

Figure 5:
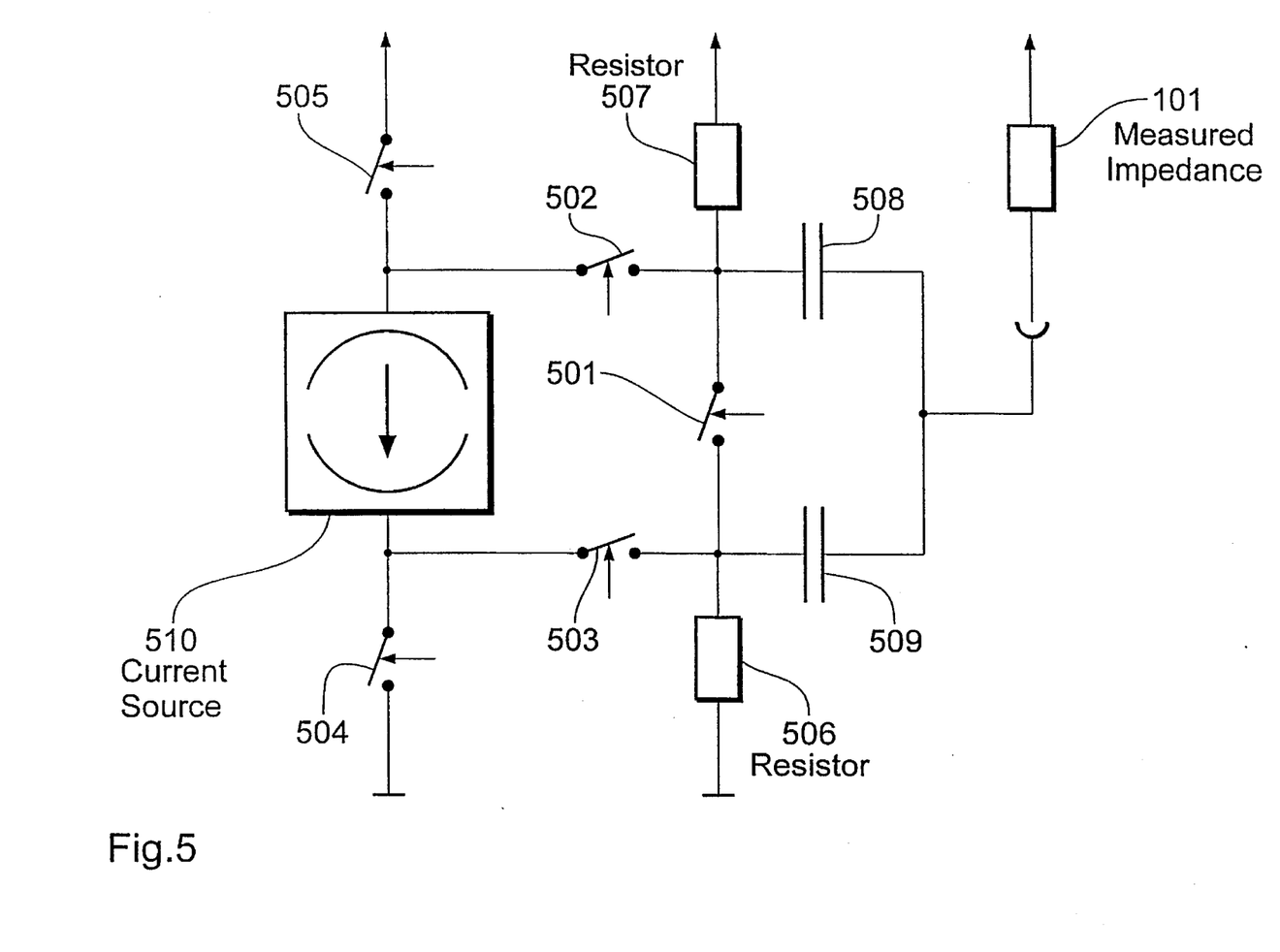
FIG. 5 a block diagram of a current source according to FIG. 1

FIG. 5 shows the block diagram of a current source of the embodiment. For clarification of the current flow, the impedance 101 to be measured is also represented.

In the resting state, i.e., without current delivery via the impedance 101, a switch 501 is closed. Further switches 502, 503, 504 and 505 are open. Two resistors 506 and 507 maintain two capacitors 508 and 509 at half of the operational voltage.

In order to deliver a positive current pulse via the impedance 101, the switch 501 is opened and the switches 503 and 505 are closed. The voltage of the capacitor 509 now lies in series with the positive operating voltage, so that the capacitor discharges via the impedance. The magnitude of the flowing current is determined by a current source 510.

In a negative current pulse, the switches 502 and 504 are closed, so that the capacitor 508 is charged via the impedance 101. Because the current source 510 again lies in series with the impedance 101 and the capacitor 508, it also determines the flowing current here.

The invention is not limited in its configuration to the preferred embodiment described above. Rather, a number of variations are conceivable which also make use of the represented solution in other types of embodiments.

What is claimed is:

1. A circuit for determining the impedance in a heart, a pacemaker electrode to which voltages are applied being disposed in the ventricle chamber of the heart, the circuit using the pacemaker electrode, the circuit comprising:

a current source operatively connected to the pacemaker electrode to apply current thereto, the current source having a current direction which can be switched;

switching means for switching the current direction of the current source;

measuring means for measuring the voltage applied to the pacemaker electrode at different measuring times; and determining means for determining a value representative of the impedance in the heart by determining a difference between the voltages applied to the pacemaker electrode at two of the different measuring times measured by the measuring means;

wherein currents having an identical magnitude but having opposite directions are applied to the pacemaker electrode by the current source which is switched by the switching means so that at the two respective measuring times the respective currents applied have opposite directions.

2. The circuit according to claim 1, further comprising control means for controlling the magnitude of the current delivered by the current source and flowing by way of the pacemaker electrode as a function of the magnitude of the difference between the voltages applied to the pacemaker electrode at the different measuring times.

3. The circuit according to claim 1, wherein the current source produces a current comprising pulse packets, wherein each of the pulse packets includes two rectangular pulses of opposite polarity that follow one another in close succession.

4. The circuit according to claim 3, wherein a time interval between the pulse packets is relatively large compared with a temporal spacing between individual rectangular pulses within one of the pulse packets.

5. The circuit according to claim 3, wherein the sequence of the individual rectangular pulses in a successive pulse packet is opposite to the sequence of individual rectangular pulses in a preceding pulse packet, whereby if a pulse packet has a sequence which is positive-negative, a successive pulse packet will have a sequence which is negative-positive.

6. The circuit according to claim 3, wherein the determining means further comprises circuit means for amplifying the voltage representative of the impedance so that the polarity thereof remains unchanged in each of the pulse packets.

7. Circuit according to claim 3, wherein, with the determining means, a difference voltage that is representative of a temporal change in impedance in the heart is formed by subtracting from a first voltage measured at a first point in time representative of the impedance at the first point in time, a second voltage measured at a second later point in time, and wherein both the first and second voltages are obtained through measurements in pulse packets that coincide in their pulse sequence.

8. The circuit according to claim 7, further comprising means for forming a sum from two difference voltages representative of the temporal change, wherein the two difference voltages are respectively obtained through measurements in pulse packet pairs that differ in their pulse sequence.

* * * * *

UNITED STATES PATENT AND TRADEMARK OFFICE
CERTIFICATE OF CORRECTION

PATENT NO. : 5,603,725
DATED      : February 18, 1997
INVENTOR(S): Max SCHALDACH It is certified that error appears in the above-indentified patent and that said Letters Patent is hereby corrected as shown below:

On the title page, item [54], change the title to read
-- CIRCUIT FOR MEASURING IMPEDANCE IN THE HEART --

Signed and Sealed this

Twenty-seventh Day of May, 1997

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,603,725
DATED : February 18, 1997
INVENTOR(S) : Max Schaldach

It is certified that error appears in the above-identified patent and that said Letters Patent is hereby corrected as shown below:

On the title page, item [73], the name of the Assignee should read

--BIOTRONIK Me$^\beta$ –und Therapiegeräte GmbH & Co. Ingenieurobüro Berlin --

Signed and Sealed this

Third Day of February, 1998

Attest:

BRUCE LEHMAN

*Attesting Officer*　　　*Commissioner of Patents and Trademarks*